(12) United States Patent
Geisel (10) Patent No.: US 10,441,343 B2
(45) Date of Patent: *Oct. 15, 2019

(54) HEATED RESONANT CUTTING DEVICE AND METHOD OF USE THEREOF

(71) Applicant: Donald J. Geisel, Clifton Park, NY (US)

(72) Inventor: Donald J. Geisel, Clifton Park, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/291,195

(22) Filed: Mar. 4, 2019

(65) Prior Publication Data

US 2019/0192210 A1    Jun. 27, 2019

Related U.S. Application Data

(63) Continuation of application No. 14/464,018, filed on Aug. 20, 2014, now Pat. No. 10,219,856.

(60) Provisional application No. 61/960,924, filed on Sep. 30, 2013.

(51) Int. Cl.
| | |
|---|---|
| A61B 18/14 | (2006.01) |
| A61B 18/12 | (2006.01) |
| A61B 18/10 | (2006.01) |
| A61B 18/08 | (2006.01) |
| A61B 18/00 | (2006.01) |

(52) U.S. Cl.
CPC ............ *A61B 18/10* (2013.01); *A61B 18/082* (2013.01); *A61B 2018/00589* (2013.01); *A61B 2018/00601* (2013.01); *A61B 2018/00607* (2013.01)

(58) Field of Classification Search
CPC .................. A61B 18/082; A61B 18/10; A61B 2018/00589; A61B 2018/00601; A61B 2018/00607
See application file for complete search history.

(56) References Cited

U.S. PATENT DOCUMENTS

| | | | |
|---|---|---|---|
| 4,116,198 A | * | 9/1978 | Roos ...................... A61B 18/12 606/46 |
| 4,600,018 A | | 7/1986 | James et al. |
| 5,611,798 A | | 3/1997 | Eggers |

(Continued)

OTHER PUBLICATIONS

Change-A-Tip Cauteries, Bovie Medical Corporation. http://www.boviemed.com/products_aaroncauteries_changeatip.asp. Printed on May 10, 2008—2 pages.

(Continued)

*Primary Examiner* — Daniel W Fowler
*Assistant Examiner* — Tigist S Demie
(74) *Attorney, Agent, or Firm* — Schmeiser, Olsen & Watts, LLP (57) ABSTRACT

Disclosed herein is a cutting and/or coagulating device that includes a cutting and/or coagulating member and a radio frequency generator such that an output of the radio frequency generator is connected to the cutting and/or coagulating member. The cutting and/or coagulating member is electrically resonant at the frequency of the radio frequency generator. Further, the cutting and/or coagulating member may include a resistance wire which is configured to directly contact a target cutting material. The cutting and/or coagulating member may be further heated to a visible glow. Furthermore, a method of cutting and/or coagulating is also contemplated.

20 Claims, 8 Drawing Sheets

(56) References Cited

U.S. PATENT DOCUMENTS

| | | |
|---|---|---|
| 8,292,879 B2 | 10/2012 | Manwaring et al. |
| 8,372,066 B2 | 2/2013 | Manwaring et al. |
| 8,377,052 B2 | 2/2013 | Manwaring et al. |
| 8,414,569 B2 | 4/2013 | Manwaring et al. |
| 8,419,724 B2 | 4/2013 | Manwaring et al. |
| 8,425,503 B2 | 4/2013 | Manwaring et al. |
| 8,430,870 B2 | 4/2013 | Manwaring et al. |
| 10,219,856 B2 | 3/2019 | Geisel |
| 2008/0119841 A1 | 5/2008 | Geisel |
| 2010/0268211 A1 | 10/2010 | Manwaring et al. |
| 2012/0226270 A1 | 9/2012 | Manwaring et al. |
| 2013/0237982 A1 | 9/2013 | Rencher et al. |
| 2014/0031785 A1 | 1/2014 | Schwagten et al. |
| 2015/0094711 A1 | 4/2015 | Geisel |

OTHER PUBLICATIONS

Cauteries, Bovie Medical Corporation. http://www.boviemed.com/products_aaroncauteries_high_asp. Printed on May 10, 2008—2 pages.

TCU: Directions for Use. Geiger Medical TCU-Product Manual. http://www.cautery.org/html.php/tcu/manual. Printed on May 10, 2008—6 pages.

Thermal Cautery with TCU-Coagulation without the Zap. Geiger Medical TCU-Product Manual. http://www.cautery.org/html.php/tcu/index. Printed on May 10, 2008—2 pages.

AW Elemental Cautery Unit. Brymill Cryogenic Systems | UK Ltd. http://www.brymilluk.com/index/php?main_page=index@cPath=5_82_83. Printed on May 10, 2008—2 pages.

Cautery Catalog. Advanced Meditech International, Inc. (AMI). http://www.ameditech.com/products/catalog/cautcat04122005.htm. Printed on May 10, 2008—11 pages.

\* cited by examiner

HEATED RESONANT CUTTING DEVICE AND METHOD OF USE THEREOF

RELATED APPLICATIONS

This application is a continuation of U.S. patent application Ser. No. 14/464,018 filed Aug. 20, 2014 entitled "Heated Resonant Cutting Device and Method of Use Thereof," which is a non-provisional application of and claims priority from U.S. Provisional Patent Application No. 61/960,924 filed Sep. 30, 2013, and entitled "Heated RF Surgical Blade"; all of which are incorporated herein by reference in their entirety.

FIELD OF TECHNOLOGY

The subject matter disclosed herein relates generally to cutting devices. More particularly, the subject matter relates to a heated resonant RF cutting device, and a method of use thereof.

BACKGROUND

There are many devices used by surgeons for the purpose of making incisions in patient tissue. These devices often use RF current supplied to a cutting probe, where current flows through patient tissue then back to a patient pad when making such incisions. These devices do not typically use heat for making an incision.

Additionally, there are many existing cautery devices which use direct current to heat up a cauterizing probe. These devices often use a resistive material, such as nichrome, for their cauterizing probe. Once current is supplied, the resistive material is configured to heat up in a similar manner to a stove or toaster wire. It usually takes a significant amount of time for these devices to both heat and cool. Furthermore, due to the nature of energy transfer, these direct current cauterizing probes often lose a significant amount of heat the instant they are brought into contact with material to be cut.

There are few prior art devices which do exist which use the principles of RF cutting probe, i.e. transferring RF across tissue to make a cut, but also apply heat. However, these known heated RF cutting devices require the transfer of a significant amount of RF current across tissue.

Thus, a heated resonant surgical blade, and method of use thereof, would be well received in the art.

SUMMARY

According to a first described aspect, a cutting and/or coagulating device comprises: a cutting and/or coagulating member; and a radio frequency generator such that an output of the radio frequency generator is connected to the cutting and/or coagulating member; and wherein the cutting and/or coagulating member is electrically resonant at the frequency of the radio frequency generator and wherein the cutting and/or coagulating member includes a resistance wire which is configured to directly contact a target cutting material.

According to a second described aspect, a cutting and/or coagulating device comprises: a resonant circuit including a cutting and/or coagulating member; and a radio frequency generator such that an output of the radio frequency generator is connected to the resonant circuit, wherein the radio frequency generator is configured to generate RF current at a frequency that is a resonant frequency of the resonant circuit during cutting and/or coagulating by the cutting and/or coagulating member, and wherein the cutting and/or coagulating member is heated to a visible glow.

According to a third described aspect, a method of cutting and/or coagulating comprises: providing RF current to a cutting and/or coagulating member at a resonant frequency of the cutting and/or coagulating member, wherein the cutting and/or coagulating member is heated to a visible glow; and cutting and/or coagulating with the cutting and/or coagulating member when the RF current is provided at the resonant frequency.

BRIEF DESCRIPTION OF THE DRAWINGS

The subject matter disclosed herein is distinctly claimed in the claims at the conclusion of the specification. The foregoing and other features and advantages are apparent from the following detailed description taken in conjunction with the accompanying drawings in which:

DETAILED DESCRIPTION

A detailed description of the hereinafter described embodiments of the disclosed apparatus and method are presented herein by way of exemplification and not limitation with reference to the Figures.

Figure 1:
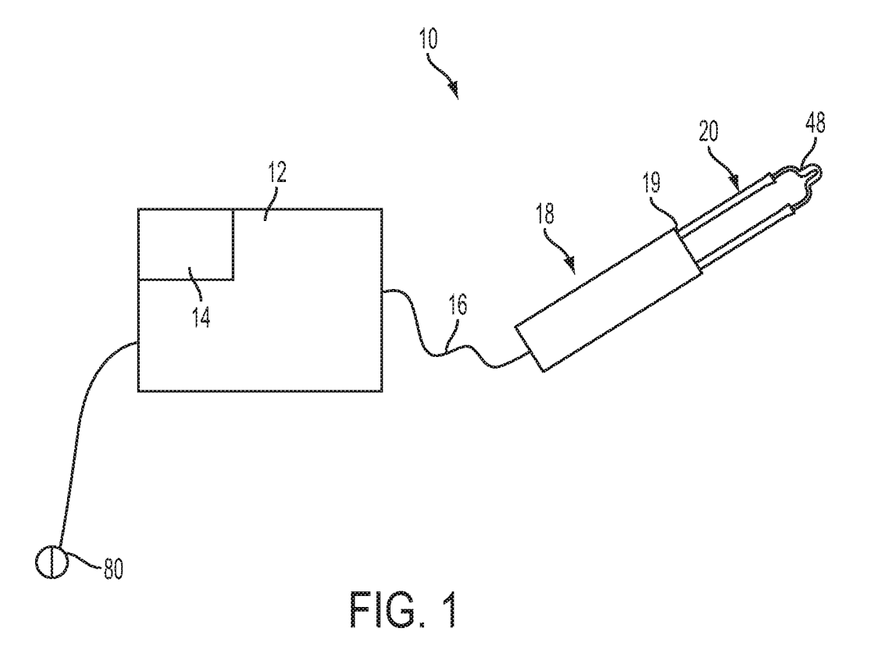
FIG. 1 depicts a perspective view of a cutting device according to one embodiment.

Referring first to FIG. 1, a cutting device 10 is shown. The cutting device 10 may herein be referred to as a cutting device, a cutting and/or coagulating device, or a coagulating device. However, it should be understood that the cutting device 10 may be utilized for both cutting and coagulation depending on the embodiment. The cutting device 10 includes a radio frequency (RF) generator 12, powered by AC or a battery 14. The output of the RF generator 12 is connected to an RF connecting cable 16. This RF connecting cable 16 is connected to a cutting probe assembly 18. A distal end 19, relative to the RF connecting cable 16, of the cutting probe assembly 18 includes a cutting head 20, with a cutting tip 48. The cutting head 20 and the cutting tip 48 may also be considered a coagulating head 20, a coagulating tip 48, or a cutting and/or coagulating head 20 and a cutting and/or coagulating tip 48. It should be understood that the cutting head 20 may be replaced with various other cutting members depending on the embodiment. Thus, an output of the RF generator 12 is connected to the cutting head 20 and to the cutting tip 48. The cutting head 20 is shown to be electrically resonant at the frequency of the RF generator 12 when connected with a resonating chip capacitor 47 to create a resonant circuit. The cutting tip 48 may be, for example, a resistance wire which is configured to directly contact a target cutting material, such as the skin or tissue of a patient. In other words, the cutting tip 48 may not include any additional ferromagnetic component that surrounds an inner member and contacts the target cutting material during cutting. The electrically resonant feature of the cutting head 20 may be configured to promote the coupling of energy into target tissue for cutting and/or coagulation. Moreover, the heat of the cutting head may be raised to a sufficient temperature, e.g. a temperature that changes the color of the cutting tip 48 to a cherry red color prior to or during cutting, to promote the coupling of energy to target tissue for cutting and coagulation.

Figure 2A:
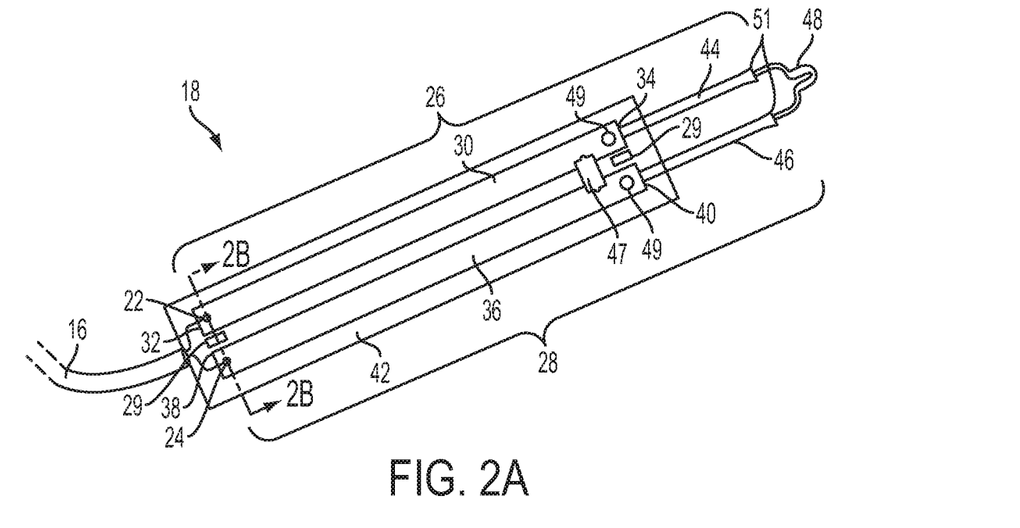
FIG. 2A depicts a perspective cutaway view of a probe assembly of the cutting device of FIG. 1 according to one embodiment.

Referring now to FIG. 2A, a perspective cutaway view of the cutting probe assembly 18 is shown. The RF connecting cable 16 may include a first contact 22 and a second contact 24. In the embodiment shown, the RF connecting cable 16 may be a coaxial cable. In this embodiment, the first contact 22 may be an inner conductor of the coaxial cable while the second contact 24 may be an outer shield conductor of the coaxial cable. In other embodiments, other types of RF wires and cables are contemplated. In the embodiment shown, the first contact 22 contacts a first metallic path 26 and the second contact 24 contacts a second metallic path 28. Each of the first and second metallic paths 26, 28 may lead to a cutting tip 48. Thus, the cutting tip 48 may be connected to each of the first metallic path 26 and the second metallic path 28. The first metallic path 26 may include a first metallic rod 30 having a first end 32 and a second end 34. The first metallic rod 30 may be attached the first contact 22 of the RF connecting cable 16 at the first end 32 of the first metallic rod 30. The second metallic path 28 may include a second metallic rod 36 having a first end 38 and a second end 40. The second metallic rod 36 may be attached to the second contact 24 of the RF connecting cable 16 at the first end 38 of the second metallic rod 36. The first and second metallic rods 30, 36 may each be located within a handle 42 of the cutting device 10. The first and second metallic rods 30, 36 may each be brass tubes or bars with a square or rectangular cross section. Alternately, the first and second metallic rods 30, 36 may not be rods at all, but may be an inner and an outer conductive component. The handle 42 may be configured to be held by a surgeon during a cutting procedure or operation. These rods 30, 36 may be separated by the insulating spacers 29 at each of the first ends 32, 38 and second ends 34, 40.

The cutting head 20 may include a first elongated metallic element 44, a second elongated metallic element 46 and the cutting tip 48. This assembly of the cutting head 20 may be removably attachable to the handle 42 as described hereinbelow. The cutting tip 48 may be attached to the ends of the first and second elongated metallic elements 44, 46. The cutting tip 48 may extend outwardly from the cutting probe assembly 18 and from the first and second elongated elements 44, 46. The first elongated metallic element 44 may be removably attachable to the second end 34 of the first metallic rod 30. Likewise, the second elongated metallic element 46 may be removably attachable to the second end 40 of the second metallic rod 36. The first and second elongated metallic elements 44, 46 may, for example, be attachable to the first and second metallic paths 26, 28 with a hex screw 49. However, other embodiments are contemplated for removable attachment such as another type of quick-release connector. This hex screw 49 or quick release connector may be configured to allow immediate and detachment of the cutting head 20 from the handle 42. Thus, a surgeon, operator or other user that is using the cutting device 10 would not need to discard the entire cutting probe assembly 18 after surgery. Rather, the surgeon may simply discard the cutting head 20, including the first elongated metallic element 44, the second elongated metallic element 46, and the cutting tip 48, and replace the cutting head 20 with a new cutting head for use in the next procedure.

The electrical current may flow through the RF connecting cable 16 to the first contact 22 through the first metallic rod 30 then to the first elongated metallic element 44, then to the cutting tip 48, then to the second elongated metallic element 46, then to the second metallic rod 36, then to the connecting cable 16 through the second contact 24.

Figure 2B:
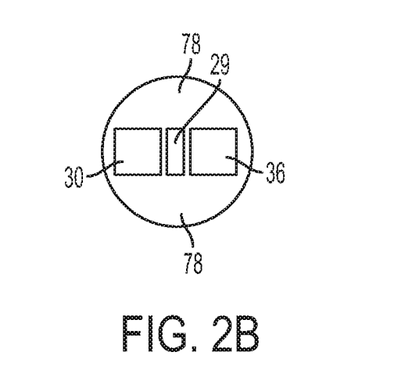
FIG. 2B depicts a cross sectional view taken at arrows 2B-2B in FIG. 2A, of the cutting probe assembly according to one embodiment.

As further shown in FIG. 2A, the resonating chip capacitor 47 is shown located and/or extending between the first metallic rod 30 and the second metallic rod 36. This resonating chip capacitor 47 may be located in electrical parallel with the cutting tip 48 to create a resonant circuit 50. The resonating chip capacitor 47 may, for example, be soldered to each of the first metallic rod 30 and the second metallic rod 36. In other embodiments, a two or more resonating chip capacitors may be used rather than the single resonating chip capacitor shown in FIG. 2. The additional resonating chip capacitor(s) may be included extending between the first and second metallic rods 30, 36 in parallel with the first resonating chip capacitor 47. It should be understood that although the resonating capacitor 47 is shown connected across the ends of the first and second metallic rods 30, 36, the capacitor 47 may be connected across the ends of the first and second elongated elements 44, 46. This alternate connection is electrically equivalent due to the immediate proximity, with both locations for chip capacitor being adjacent to distal end 19.

In one embodiment, the cutting tip 48 of the cutting head 20 may be an iron resistance wire. Similarly, the first metallic path 26 and the second metallic 28 path may each primarily be made from brass. For example, the first metallic rod 30 and the second metallic rod 36 may each be made from brass. Similarly, the first elongated metallic element 44 and the second elongated metallic element 46 may also be made from brass. Other materials are contemplated for the material components. For example, the cutting tip 48 may also be made from nickel, chrome, nickel chrome, silicon carbide, steel, stainless steel, tungsten or combination(s) thereof. Similarly, the components of the first and second metallic paths 26, 28 may be made from copper, silver, aluminum, other good conductors or combination(s) thereof.

Figure 3:
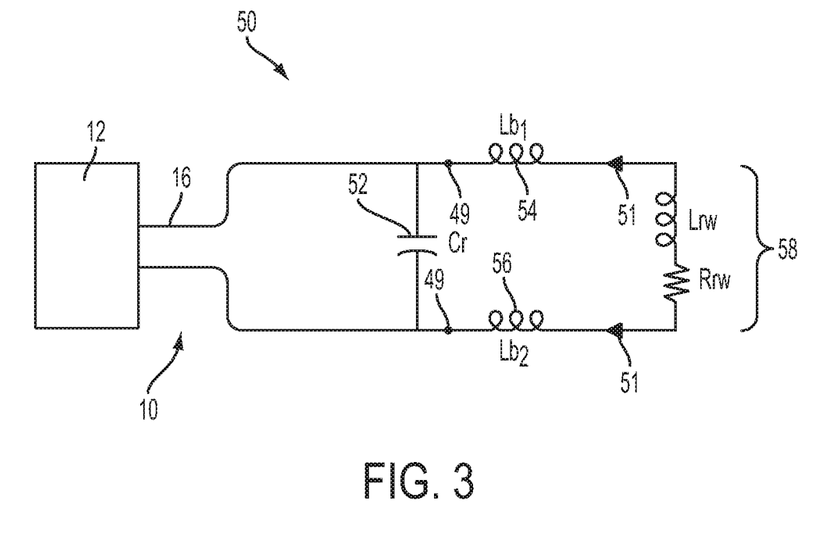
FIG. 3 depicts an equivalent electrical circuit depicting the cutting device of FIGS. 1-2B according to one embodiment.

Referring now to FIG. 3, an equivalent electrical circuit of the cutting device 10 is shown. The cutting device 10 includes the RF generator 12 for generating power through the RF connecting cable 16 to a resonant circuit 50. It should be understood that the resonant circuit 50 may include some or all of the components of the cutting probe assembly 18 along with the cutting head 20. As shown in FIG. 3, the resonant circuit 50 may include a resonating capacitor 52, a first inductor 54, a second inductor 56 and an inductor and resistor combination element 58. FIG. 3 further shows the hex screws 49 and the connecting crimps 51, as originally shown in FIG. 2A. It should be understood that the first inductor 54 and the second inductor 56 may represent the first elongated metallic element 44 and the second elongated metallic element 46 of the cutting probe assembly 18. Likewise, the inductor and resistor combination element 58 may represent the resistance wire of the cutting tip 48, which may include resistive and inductive qualities. The inductor and resistor combination element 58 may be located in a parallel configuration with the resonating capacitor 52. The series inductance of the first and second inductors 54, 56 (i.e. the first and second elongated metallic elements 44, 46) is Lb1 and Lb2. The series inductance of the cutting tip 48 is Lrw and the resistance loss of the cutting tip 48 is Rrw.

It should be understood that parallel resonance occurs when the reactance of the resonating capacitor 52, Cr, equals the reactance of the sum of the circuit inductance, Lsum. The sum of the circuit inductance, Lsum=Lb1+Lb2+Lrw, at the frequency of the RF generator. In one embodiment, the frequency of the RF generator may be between 24 and 30 Mhz. This may be the frequency which is electrically resonant in the cutting head. In one embodiment, the resonant frequency may be 27 Mhz. It should be understood, however, that the RF generator may generate power between 0.5 MHz and 900 MHz or any power at a radio frequency. In one embodiment, the RF generator 12 may provide power of 10 watts. In other embodiments, more or less power, for example between 1 and 100 watts, may be necessary to heat the cutting head 20 as desired at the resonant frequency. The exemplary embodiments described hereinabove may have impedance having a phase angle near zero. This may make the exemplary embodiment described hereinabove as a good match to a 50 ohm coaxial cable while minimizing loss. Thus, the cutting device 10 described herein may include a cutting head 20 which resonates at a frequency provided by the RF generator 12 when connected in parallel with the resonating chip capacitor 47. However, the coaxial cable 16 may specifically not resonate at the resonant frequency of the resonant circuit 50 and may not be resonating during the heating and cutting of the cutting head 20. The benefits of a non-resonant connecting cable 16, for example, may be avoiding high resonance currents and voltages on the cable, thus avoiding excessive losses, heat and stray coupling of RF to surgeons and/or a patient.

Figure 4:
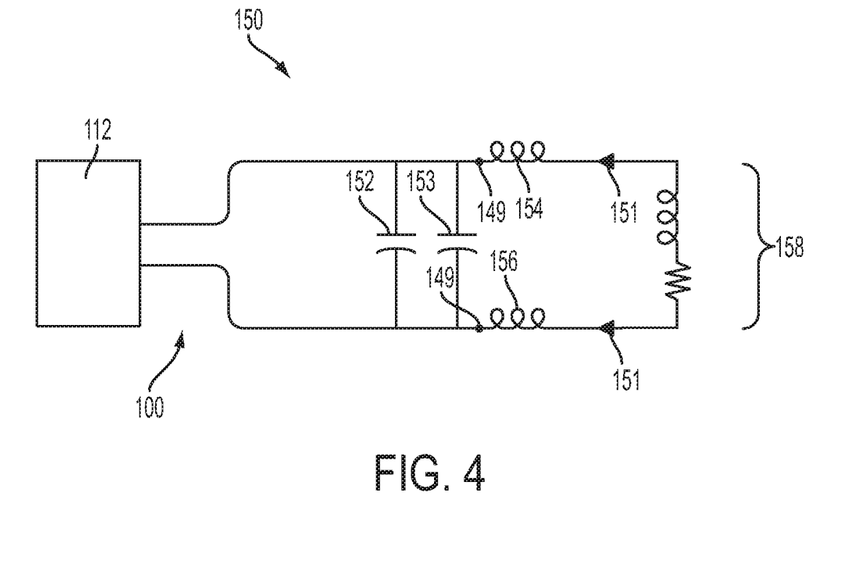
FIG. 4 depicts an equivalent electrical circuit depicting an alternate cutting device according to one embodiment.

FIG. 4 shows another equivalent electrical circuit of another embodiment of a cutting device 100 similar to the cutting device 10 having a resonant circuit 150 and an RF generator 112. However, the cutting device 100 includes a resonant circuit with two resonating capacitors 152, 153, rather than one, in addition to a first inductor 154, a second inductor 156 and an inductor and resistor combination element 158. FIG. 4 further shows hex screws 149 and connecting crimps 151. These may be the same or similar to the hex screws 49 and connecting crimps 51 shown in the embodiment from FIG. 2A. These resonating capacitors 152, 153 may each be attachable in parallel to the metallic rods (not shown) in the same manner described hereinabove. In other words, several resonating capacitors 152, 153 may be placed in parallel to achieve the correct value of the reactance, Cr. Thus, it should be understood that other resonating circuit equivalents are contemplated which include various components which operate to form simple or complex RLC circuits or LC circuits in parallel or series configurations.

Figure 5:
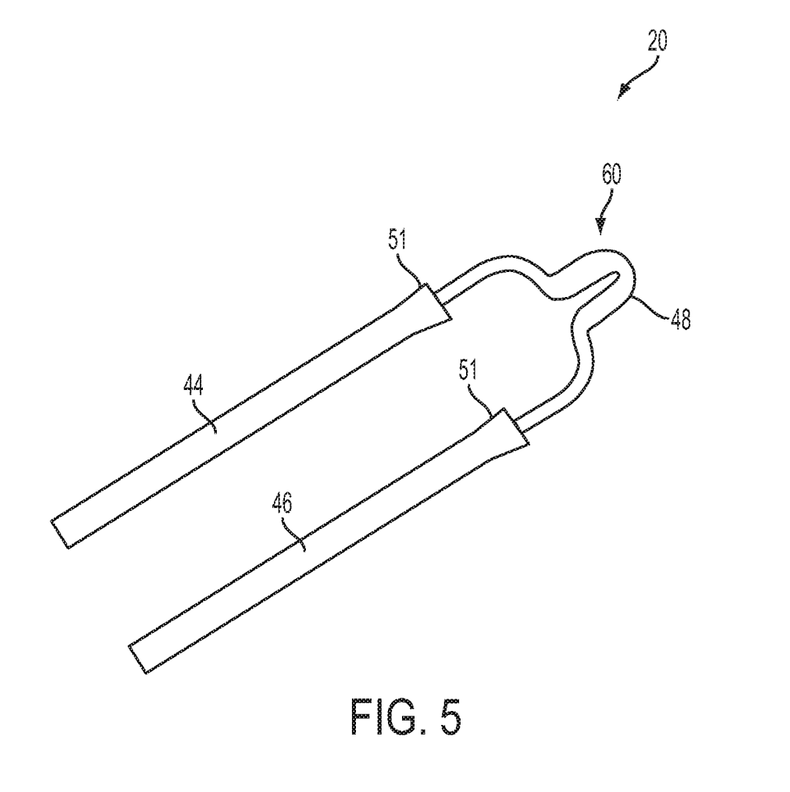
FIG. 5 depicts an expanded perspective view of a cutting head of the cutting device of FIGS. 1-3.

Referring now to FIG. 5, the cutting head 20 may include the cutting tip 48 that is bent in a particular manner in order to facilitate cutting. The cutting tip 48 may be made of iron resistance wire, for example, and may have a diameter between 0.001 inches and 0.1 inches. In one embodiment, the diameter of the resistance wire of the cutting tip 48 may be 0.015 inches. The cutting tip 48 may include a narrow portion 60 that is sharpened with a diamond grinder. The cutting tip 48 may be shaped in numerous forms to promote the transfer of RF and for the convenience of the surgeon, operator, or user. The cutting tip 48 may take various shapes and the thickness of the cutting tip 48 and cross sectional dimensions may vary. Thicker and thinner cross sections are contemplated.

Figure 6A:
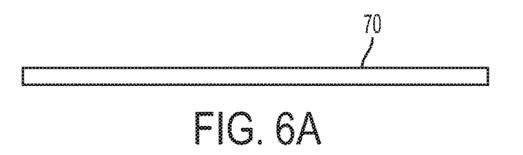
FIG. 6A depicts a perspective view of a resistance wire prior to being fashioned into the cutting head of FIG. 4 according to one embodiment.
Figure 6B:
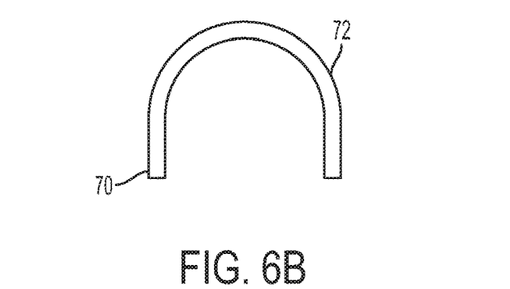
FIG. 6B depicts a perspective view of the resistance wire of FIG. 6A after being bent with a loop according to one embodiment.
Figure 6C:
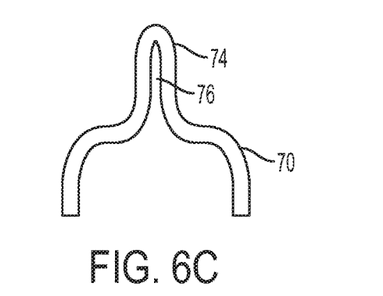
FIG. 6C depicts a perspective view of the resistance wire of FIGS. 6A-6B after being compressed at a tip according to one embodiment.
Figure 6D:
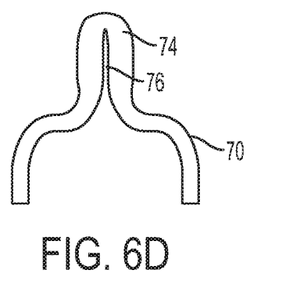
FIG. 6D depicts a perspective view of the resistance wire of FIG. 6a-6c after being compressed at a cross section at the tip according to one embodiment.
Figure 6E:
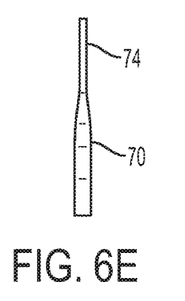
FIG. 6E depicts a side profile view of the resistance wire of FIG. 6D-1 according to one embodiment.
Figure 6F:
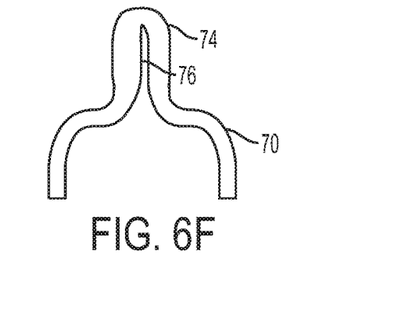
FIG. 6F depicts a perspective view of the resistance wire of FIGS. 6a-6d after a tip being ground with a diamond grinder according to one embodiment.

FIGS. 6A-6E show an embodiment for steps of fashioning the cutting tip 48. The fashioning of the cutting tip 48 may first begin with a length of 0.015 outer diameter resistance wire 70 as shown in FIG. 6A. First, this resistance wire 70 may be compressed to form a wide curl 72, as shown in FIG. 6B. Next this resistance wire 70 may be compressed, squeezed or otherwise fashioned at the apex of the wide curl 72 into a tighter tip 74, as shown in FIG. 6C. FIG. 6C shows that, after squeezing the tip 74 together, an extremely small gap 76 exists between the tip 74. FIGS. 6D and 6E each show the tip 74 after having been compressed in a cross-sectional manner into a flat portion. This flat tip may include a thickness, for example, of 0.008 inches. At this point, the tip 74 includes a gap 76 having a thickness of 0.001 inches, for example. The final stage of the formation of the cutting tip 48 may include a diamond grinder (not shown) being used to shave away metal from each side of the tip 74. The diamond grinder may be used to shave more from one side of the tip 74 than the other. The right side of the tip 74 in the embodiment shown is has a more reduced thickness, as shown in FIG. 6F. Both the side-by-side location of both sides of the tip 74 and the grinding by the diamond grinder may create a hot zone for smoother cutting of the cutting head 20 of the cutting device 10. In the end, the tip 74 may be ⅒ or about ⅒ the length of the total length of the resistance wire 70. Moreover, the tip 74 may be fashioned or cut with other techniques. The steps described hereinabove, or any other technique used for the formation of these cutting tips 48 may be created with an automated assembly system.

The cutting tip 48 may thereby be fashioned or integrated into the cutting head 20 by attaching the cutting tip 48 to the first and second elongated metallic elements 44, 46. These first and second elongated metallic elements 44, 46, may, for example, be hollow and tubular and may have a small outer diameter such as, for example, 1/32 inches. The ends of cutting tip 48 may be inserted within the hollow tubular rods 44, 46, respectively. Once the ends of the cutting tip 48 are inserted within the tubular rods 44, 46, the ends tubular rods 44, 46 may be crimped into crimps 51 or otherwise compressed to permanently flatten the ends and thereby attach the tubular rods 44, 46 to the two ends of the cutting tip 48.

The small dimensions of the first and second elongated metallic elements 44, 46 with respect to the first and second metallic rods 30, 36 may limit excessive heat flow from returning into the handle 42 from the first and second elongated metallic elements 44, 46. As shown in the cross sectional view shown in FIG. 2B, the heat which does transfer into the handle 42 via the first and second metallic rods 30, 36 is further conducted away through the first and second metallic rods 30, 36 and additionally cooled by convection cooling form an air gap 78 located above and below the first and second metallic rods 30, 36. This air gap 78 resides from excess space on the inside diameter of the handle 42 and the combined inner assembly of the first and second metallic rods 30, 36. Moreover, a vacuum line may be utilized in the air gap 78 to further increase convection cooling by pulling warm air from the cutting probe assembly 18 and the interior assembly of the first and second metallic rods 30, 36. Still further, another means of cooling may be dripping sterile water or saline on the first and second elongated metallic elements 44 and 46 during or after use of the cutting device 10. This cooling means may require a low pressure delivery tube which would be located in the air gap 78. It should be understood that the cross sectional shape of the handle 42 may be circular as shown. In other embodiments, the handle 42 may be ovular, rectangular or square to provide more or less space for the air gap 78 as necessary. Furthermore, it should be understood that the handle 42 may be made from a nonmetallic material.

In one embodiment, a protective end cover (not shown) may be utilized to protect the cutting head 20. The protective end cover may be retractable from the cutting head when the cutting head is in use for an operation or procedure. This protective end cover may protect the cutting head 20 from damage or being bent when not in use. Moreover, the protective end cover may protect adjacent objects from thermal damage after an operation or procedure in the immediate time frame before the cutting head 20 is cooled.

The cutting tip 48 may be protected from oxidation or corrosion in one embodiment with a thin protective layer. Materials such as ceramic, porcelain enamel or glass like material of 1 mil (0.001 inch) thickness or less may be employed. This material may be applied to the cutting tip 48 either before or after the cutting tip 48 is fashioned from the resistance wire into the shape of the cutting tip 48. Additionally, a very thin layer of aluminum may be applied and heated to bond or partially diffuse into the iron base layer. Other noble metals may function in a similar manner to the aluminum.

The cutting tip 48 described herein may be configured to be heated to temperatures ranging from 1500 F or higher. As described hereinabove, the cutting tip 48 may be heated such that it changes color to become cherry red, occurring above 1650 F, for example, for materials like iron or steel. In other embodiments, the cutting tip 48 may change to a dull cherry red (1450 F or more) or a bright cherry red (1800 F or more). In other embodiments, the temperature may be sufficiently high to create a visible glow in the cutting tip 48. Still further, even brighter glows such as orange glows, occurring at over 2000 F are contemplated. It should be understood that the curie temperature of iron is 1418 F. Embodiments contemplated herein may all be configured to reach temperatures which are substantially greater than this curie temperature. This may facilitate cutting and promote the coupling of energy to target tissue for cutting and coagulation. Furthermore, it should be understood that the melting temperature for iron is about 2800 F. Temperatures may thus remain below this melting temperature during the cutting process. The cutting device 10 may further be configured with temperature settings which are configured to set the temperature of the cutting probe when cutting. For example, a toggle may provide for the dynamic change in temperature across a wide spectrum. Alternately, the cutting device 10 may contain pre-programmed modes which each provide for set cutting temperatures (for example, 1600 F, 1800 F, 2000 F and 2200 F). These modes may be accessible via an interface found on the RF generator 12 box.

The heating and cooling of the cutting head 20 may take place in a matter of seconds. For example, once power is supplied to the cutting head 20 at the resonant frequency, the cutting head 20 may be heated in less than 5 seconds. Once power is removed from the cutting head 20, the cutting head 20 may cool in less than 5 seconds. In one embodiment, the heating and cooling occurs in less than two seconds. Furthermore, the cutting head 20 may be considered cooled when a person is able to touch the cutting head without being burned or harmed.

Referring back to FIG. 1, the heating and cooling of the cutting head 20 may be accomplished with a foot pedal 80, for example. Thus, a surgeon, operator or other person using the cutting device 10 may apply heat to the cutting head 20 in a hands free manner. The foot pedal 80 may further include multiple buttons depending on the embodiment. For example, if the cutting device 10 includes other functionality such as a coagulating forceps attachment (not shown), the surgeon could use the foot pedal to switch from applying power to the cutting head 20 and the coagulating forceps. Alternatively, miniature switches may be incorporated into the cutting probe handle, 42 to accomplish functions identical to the pre discussed foot switch.

Figure 7A:
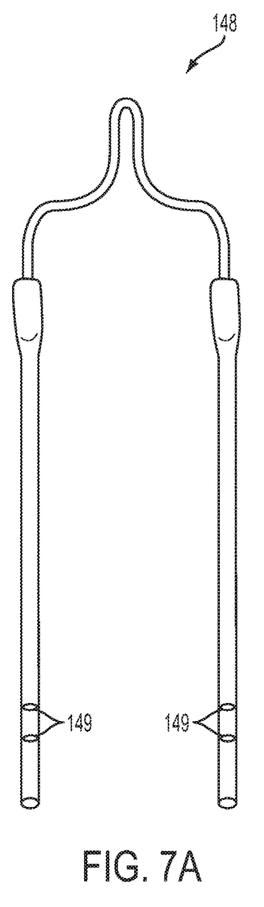
FIG. 7A depicts a perspective view of a different cutting tip component according to one embodiment.
Figure 7B:
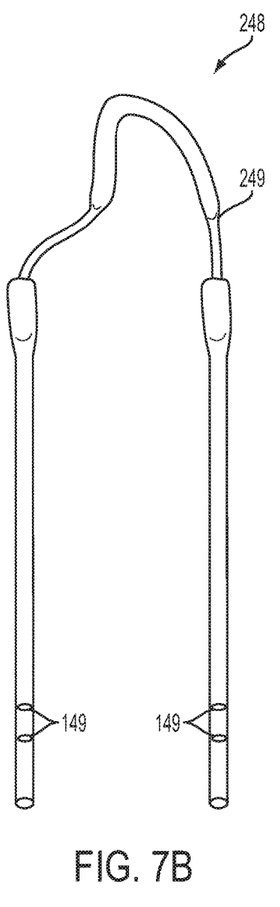
FIG. 7B depicts a perspective view of a different cutting tip component according to one embodiment.
Figure 7C:
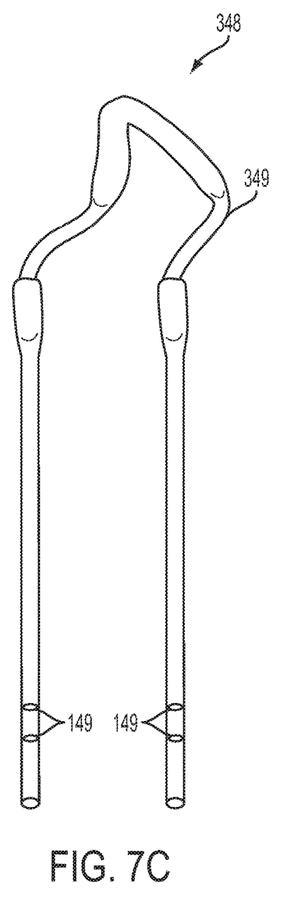
FIG. 7C depicts a perspective view of a different cutting tip component according to one embodiment.
Figure 7D:
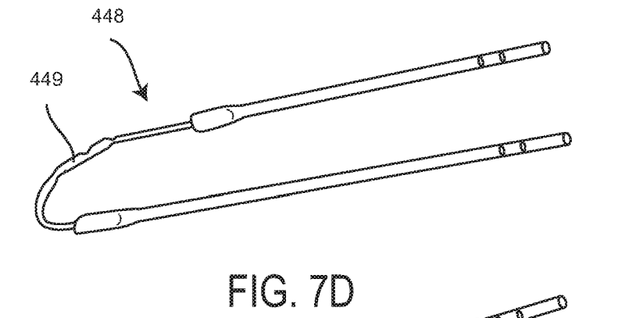
FIG. 7D depicts a perspective view of a different cutting tip component according to one embodiment.
Figure 7E:
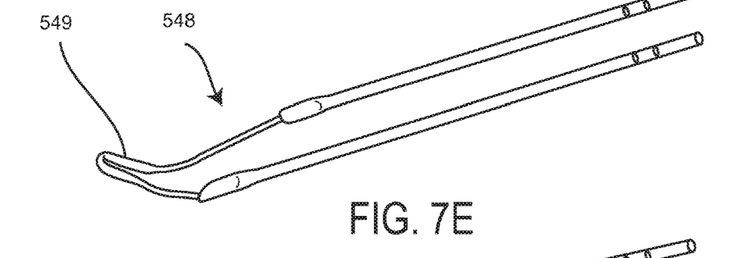
FIG. 7E depicts a perspective view of a different cutting tip component according to one embodiment.
Figure 7F:
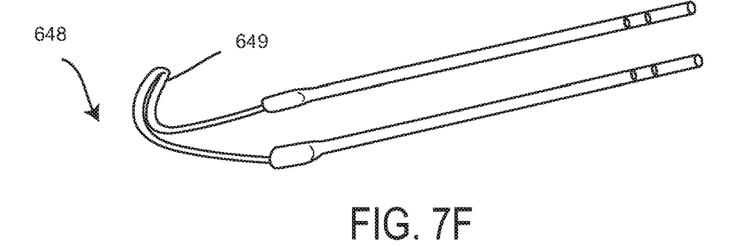
FIG. 7F depicts a perspective view of a different cutting tip component according to one embodiment.
Figure 7G:
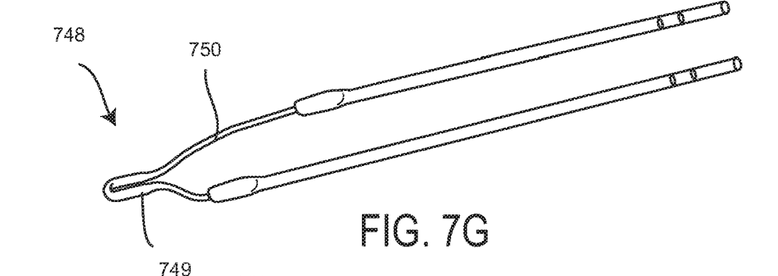
FIG. 7G depicts a perspective view of a different cutting tip component according to one embodiment.
Figure 7H:
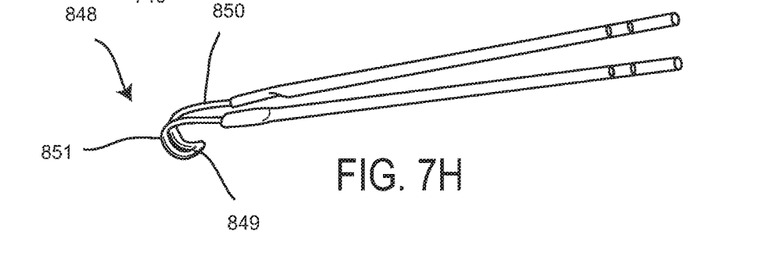
FIG. 7H depicts a perspective view of a different cutting tip component according to one embodiment.

Referring now to FIGS. 7A-7H, several embodiments of differently shaped cutting tips of a cutting head 20 are contemplated. A first cutting tip 148 is shown in FIG. 7A which has a larger gap between the left and right sides of the cutting tip 148 than the cutting tip 48. A second cutting tip 248 is shown in FIG. 7B that includes a smooth curved cutting surface 249. A third cutting tip 348 is shown in FIG. 7C that includes an angled cutting surface 349. It should be understood that the shapes of the cutting surface 48, 148, 248, 348 are exemplary and that other cutting tips 348 are contemplated. The cutting device 10 may include a plurality of different detachably attachable cutting heads 20 that can be applied in various different cutting situations as necessary. A fourth cutting tip 448 is shown in FIG. 7D which includes a wide loop 449 for cutting. A fifth cutting tip 548 is shown in FIG. 7E which includes a differently shaped curve 549 for cutting, which bends in two planes. In other words, the tip 549 may actually bend out of the page in the view shown in order to facilitate cutting. In yet another embodiment shown in FIG. 7F, a sixth cutting tip 648 is shown which includes a longer hook 649 which bends in one direction. This longer hook 649 is on plane with the rest of the tip component 648 and is not curved in two planes. A seventh cutting tip 748 shown in FIG. 7G includes a similar shape to the cutting tip 48. However, a first length 750 of the cutting tip 748 is shorter than a second length 751. An eighth cutting tip 848 is shown in FIG. 7H includes a pointed cutting hook 849 which is actually curved in two planes. In other words, a first length 850 of the cutting hook 849 rests below a second length 851 of the cutting hook 849.

In other embodiments, the resonant circuit may include a pair of forceps (not shown) to replace the cutting tip components described hereinabove. The forceps may be employed for cutting and/or coagulation and may operate in the manner described hereinabove with respect to the cutting tip. A heated portion of the forceps may be located on one jaw of the forceps or both jaws of the forceps. The forceps may be energized and subsequently squeezed onto target tissue.

In still another embodiment, the resonant circuit described hereinabove may be used in conjunction with a conventional monopolar or bipolar electrical device. In the case of a monopolar device, a conventional RF generator with a frequency of, for example, 0.5 MHz, may employ a patient pad connected to its second output and the first generator output may be coupled to the resonant circuit and cutting tip for cutting and coagulation. Likewise, a conventional RF generator may be connected with its output across the tips of bipolar forceps with one tip being a resonant element in a similar manner to the resonant cutting tips described hereinabove. The conventional generator and forceps resonant element may both be energized and subsequently squeezed onto target tissue.

In another embodiment, a method of cutting and/or coagulating is contemplated. The method may include providing RF current to a cutting head, such as the cutting head 20 at a resonant frequency of the cutting head such that the temperature of the cutting head results in the color of the cutting head changing to a cherry red color. The method may further include cutting tissue with the cutting head when the RF current is provided at the resonant frequency. The method further may include providing a resistance wire as the cutting head and contacting target cutting material during the cutting. Still further, the method includes resonating the cutting head at a frequency at or about 27 Mhz. The method may include coagulating tissue with the cutting head. The coagulating may, for example, be used to stop a bleeding tissue from continuing to bleed by applying energy from the cutting head to the tissue. In one embodiment, the cutting head may be applied in a manner such that a flatter portion of the cutting head is applied such that cutting is not enacted by the application of the head. The method may further include heating the cutting head with the resonant current. The method may further include cooling the cutting head to a safe temperature to touch in five seconds or less.

Elements of the embodiments have been introduced with either the articles "a" or "an." The articles are intended to mean that there are one or more of the elements. The terms "including" and "having" and their derivatives are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

I claim:

1. A cutting and/or coagulating device comprising:
   a cutting and/or coagulating member; and
   a radio frequency generator such that an output of the radio frequency generator is connected to the cutting and/or coagulating member; and
   wherein the cutting and/or coagulating member is electrically resonant at a frequency of the radio frequency generator and wherein the cutting and/or coagulating member includes a resistance wire which is configured to directly contact a target cutting material.

2. The cutting and/or coagulating device of claim 1, wherein an electrically resonant feature of the cutting and/or coagulating member promotes coupling of energy into target tissue for cutting and/or coagulation.

3. The cutting and/or coagulating device of claim 1, wherein the cutting and/or coagulating member is heated to a temperature that promotes the coupling of energy into target tissue for cutting and/or coagulation.

4. The cutting and/or coagulating device of claim 1, wherein the cutting and/or coagulating member includes iron resistance wire.

5. The cutting and/or coagulating device of claim 1, further comprising a connecting cable extending from the radio frequency generator, the connecting cable including a first contact and a second contact, the first contact contacting a first metallic path, the second contact contacting a second metallic path, wherein a cutting and/or coagulating tip of the cutting and/or coagulating member is connected to each of the first metallic path and the second metallic path.

6. The cutting and/or coagulating device of claim 5, wherein the first metallic path and the second metallic path are each made of at least one of brass, copper and aluminum.

7. The cutting and/or coagulating device of claim 5, wherein the first metallic path includes a first metallic rod having a first end and a second end, wherein the first metallic rod is attached to the first contact of the connecting cable at the first end of the first metallic rod, wherein the second metallic path includes a second metallic rod having a first end and a second end, wherein the second metallic rod is attached to the second contact of the connecting cable at the first end of the second metallic rod, and wherein the first and second metallic rods are located in a handle of the cutting and/or coagulating device and extend across at least a majority of a length of the handle.

8. The cutting and/or coagulating device of claim 7, wherein the cutting and/or coagulating member includes a first elongated metallic element, a second elongated metallic element and the cutting and/or coagulating tip, and wherein the cutting and/or coagulating tip is attached to and extends across the first and second elongated metallic elements, wherein the first elongated metallic element is removably attachable to the second end of the first metallic rod and the second elongated metallic element is removably attachable to the second end of the second metallic rod.

9. The cutting and/or coagulating device of claim 4, wherein the cutting and/or coagulating member includes a portion that is altered mechanically by a removal of material, and wherein the iron resistance wire has a diameter between 0.01 inches and 0.018 inches.

10. The cutting and/or coagulating device of claim 1, wherein the frequency which is electrically resonant in the cutting member is between 24 and 30 MHz.

11. The cutting and/or coagulating device of claim 1, wherein a resonating capacitor is placed in parallel with the cutting member.

12. The cutting and/or coagulating device of claim 1, wherein the radio frequency generator provides a power of at least 10 watts.

13. The cutting and/or coagulating device of claim 3, wherein the temperature of the cutting and/or coagulating member causes a visible glow to at least a portion of the cutting and/or coagulating member.

14. A cutting and/or coagulating device comprising:
a resonant circuit including a cutting and/or coagulating member; and
a radio frequency generator such that an output of the radio frequency generator is connected to the resonant circuit, wherein the radio frequency generator is configured to generate RF current at a frequency that is a resonant frequency of the resonant circuit during cutting and/or coagulating by the cutting and/or coagulating member, and wherein the cutting and/or coagulating member is heated above a Curie temperature.

15. The cutting and/or coagulating device of claim 14, wherein the cutting and/or coagulating member includes resistance wire which is configured to directly contact a target cutting material.

16. The cutting and/or coagulating device of claim 14, wherein the resonant circuit of the cutting and/or coagulating member promotes the coupling of energy into target tissue for cutting and/or coagulation.

17. The cutting and/or coagulating device of claim 14, wherein the frequency which is electrically resonant in the cutting and/or coagulating member is between 24 and 30 MHz.

18. The cutting and/or coagulating device of claim 14, wherein the cutting and/or coagulating member is removably attachable to a handle of the cutting and/or coagulating device.

19. The cutting and/or coagulating device of claim 14, wherein a resonating capacitor is placed in parallel with the cutting and/or coagulating member.

20. The cutting and/or coagulating device of claim 15, wherein the cutting and/or coagulating member includes a portion that is altered mechanically by a removal of material, and wherein the resistance wire has a diameter between 0.01 inches and 0.02 inches.

* * * * *